United States Patent [19]

Tautvydas

[11] Patent Number: 5,795,730
[45] Date of Patent: Aug. 18, 1998

[54] RAPID READ-OUT BIOLOGICAL INDICATOR

[75] Inventor: Kestutis J. Tautvydas, Lake Elmo, Minn.

[73] Assignee: Minnesota Mining and Manufacturing Company, St. Paul, Minn.

[21] Appl. No.: 669,548

[22] PCT Filed: Feb. 15, 1995

[86] PCT No.: PCT/US95/01984

§ 371 Date: Jul. 12, 1996

§ 102(e) Date: Jul. 12, 1996

[87] PCT Pub. No.: WO95/21936

PCT Pub. Date: Aug. 17, 1995

[51] Int. Cl.$^6$ ............... C12Q 1/22; C12Q 1/02; C12Q 1/18; C12N 1/00
[52] U.S. Cl. ............... 435/31; 435/29; 435/839; 435/832; 435/4; 435/32; 435/808; 435/807; 435/252.5
[58] Field of Search ............... 435/31, 29, 839, 435/832, 4, 32, 808, 807, 252.5

[56] References Cited

U.S. PATENT DOCUMENTS

| | | | |
|---|---|---|---|
| 3,661,717 | 5/1972 | Nelson | 195/103.5 R |
| 4,839,291 | 6/1989 | Welsh et al. | 435/296 |
| 5,073,488 | 12/1991 | Matner et al. | 435/31 |
| 5,252,484 | 10/1993 | Matner et al. | 435/288 |

OTHER PUBLICATIONS

Dadd et al., "Germination of Spores of *Bacillus subtilis* var. *niger* Following Exposure to Gaseous Ethylene Oxide", *Journal of Applied Bacteriology*, 60, pp. 425–433, 1986.

Foster et al., "Pulling the Trigger: The Mechanism of Bacterial Spore Germination", *Molecular Microbiology*, 4(1), pp. 137–141, 1990.

Fred et al., The Reduction of 2,3,5-Triphenyltetrazolium Chloride by *Penicillium chrysogenum*, *Science*, vol. 109, pp. 169–170, Feb. 18, 1949.

Hanlon et al., "Quantitative Assessmemt pf Sterilization Efficiency Using lyophilized Calcium Alginate Biological Indicators", *Letters in Applied Microbiology*, 17, pp. 171–173, 1993.

(List continued on next page.)

*Primary Examiner*—Louise Leary

[57] ABSTRACT

This invention relates to methods and the use of biological indicator systems to assess and determine the effectiveness of sterilization processes comprising the steps of contacting an indicator comprising microbial spores with a sterilant; a medium selected to germinate the spores; and calculating a germination rate of the exposed spores to determine the effectiveness of the sterilization process. A method for rapidly determining the effectiveness of the gemination rate of microbial spores with spore viability is also described.

6 Claims, 11 Drawing Sheets

OTHER PUBLICATIONS

Parisi et al., "Sterilization with Ethylene Oxide and Other Gases", *Disinfection, Sterilization, and Preservation*, Fourth Edition, Chapter 33, pp. 580–595, 1991.

Pflug et al., "Principles of the Thermal Destruction of Microorganisms", *Disinfection, Sterilization, and Preservation*, Fourth Edition, Chapter 6, pp. 85–128, 1991.

Reich, Robert R., "Effect of Sublethal Ethylene Oxide Exposure on *Bacillus subtilis* Spores and Biological Indicator Performance", *Journal of the Parenteral Drug Association*, vol. 34, No. 3, 1980, pp. 200–211.

Rodriguez et al., "Use of a Fluorescent Redox Probe for Direct Visualization of Actively Respiring Bacteria", *Applied and Environmental Microbiolgy*, vol. 58, No. 6, pp. 1801–1808, Jun. 1992.

Spicher, "Sterilization—The Microbiology Between Claim and Reality", Zbl. Hyg., 194, pp. 223–235, 1993.

Spicher et al., "How Many Biological Indicators Have to be Tested to Make a Reliable Statement as to Their Resistance?", *Zbl. Bakt.Hyg.*, I. Abt. Orig. B 179, pp. 365–380, 1984.

Stellmach et al., "A Flourescent Redox Dye. Influence of Several Substrates and Electron Carriers on the Tetrazolium Salt—Formazan Reaction of Ehrlich Ascites Tumour Cells", *Histochemical Journal* 19, pp. 21–26, 1987.

Trevors, "Electron Transport System Activity in Soil, Sediment, and Pure Cultures", CRC *Critical Reviews in Microbiology*, vol. II, Issue 2, pp. 38–101, 1984.

Umeda et al., "Spore Outgrowth and the Development of Flagella in *Bacillus subtilis*", *Journal of General Microbiology*, 118, pp. 215–221, 1980.

Urban et al., "Nitroublue Tetrazolium (NBT) Reduction by Bacteria", *Acta path, microbiol scand.* Sect. B, 87, pp. 227–233, 1979.

RAPID READ-OUT BIOLOGICAL INDICATOR

This invention is generally related to both apparatus and methods which use biological indicators to assess or determine the effectiveness of sterilization processes and particularly relates to a rapid method of determining the effectiveness of a sterilization process by correlating a measurement of the germination rate of microbial spores with spore viability.

BACKGROUND

Biological indicators have been used to test and/or determine the effectiveness of sterilization processes. Typically, biological indicators containing microbial spores are exposed to a selected sterilant or sterilizing process and then the survival of any exposed spores is determined by placing the exposed spores in an environment capable of sustaining germination of spores and growth of microbes. In view of the fact that microbial spores are accepted as being much more resistant to sterilization processes than most other types of microorganisms, it is assumed that a sterilization process that will kill microbial spores will also kill any other contaminating microorganisms. See, e.g., *Disinfection, Sterilization, and Preservation*, Fourth Edition, ed. Block, Seymour S., Lea & Febiger, Chapter 6 (1991) that reports general criteria needed to analyze or assess sterilization processes.

Commonly used biological indicators, due to the need to allow sufficient time for spore outgrowth, have generally required extended periods of incubation time before the effectiveness of a sterilization process may be evaluated. For example, some commercially available indicators require incubation times of 1–2 days before an evaluation of the effectiveness of a sterilization process is available. The reliability of these types of biological indicators is based on a correlation of the results provided by these indicators with the number of spore survivors which are observed after seven days of growth.

The need for a more rapid determination has led to apparatus and procedures which provide an indication of sterilization effectiveness in less time. For example, U.S. Pat. Nos. 5,073,488 and 5,252,484 report methods and apparatus, respectively, that determine the efficacy of a sterilization process in a few hours by assaying microbial enzyme activity that may be correlated with spore or cell viability. In another example, U.S. Pat. No. 5,366,872 reports an assay of certain microbial enzymes in a biological indicator that gives a colored, visually detectable signal that may be related to viable bacteria or microorganisms in a sample after exposure to a sterilization cycle.

Although cell viability after exposure to a variety of sterilants and/or sterilization processes is a traditional measure of sterility, as pointed out above, the effects of such sterilants or sterilization processes on other types of microbial activity has also been investigated. Enzymatic activity has been used to determine the efficacy of a sterilization cycle. In addition, the expression of microbial spore viability, i.e., cell viability, is preceded by spore germination. Spore germination is an irreversible complex series of biochemical events occurring in the first twenty to thirty minutes after microbial spores are exposed to conditions that will support growth of the microbe. In particular, it is believed that germination may be triggered by the presence of specific germinants in the environment. See, e.g., Foster et al., *Molec. Biol*, 4:137–141 (1990) and Umeda et al., *J. Gen. Microbiol.*, 118:215–221 (1980).

Characteristically, as spores germinate, they absorb water and lose the capability of scattering light in spore-containing suspensions. This property allows germination processes to be followed spectrophotometrically as either a decrease in light absorption or a decrease in light scattering. Specifically, Dadd et al., *Journal of Applied Bacteriology*, 60:425–433 (1986) have investigated the effects of ethylene oxide sterilization cycles on the germination of *Bacillus subtilis* spores. Dadd et al. report that Bacillus spores exposed to lethal doses of ethylene oxide do not stop germinating in the presence of specific germinants even though outgrowth of Bacillus bacteria from such exposed spores does not occur. Further, these workers note that different types of media provide different percentages of germinating spores. They also found that spores exposed to ethylene oxide lose the ability to germinate but that this loss occurs at a lower rate than loss of cell viability. This report indicates that both the number of spores that germinate as well as the number of viable spores may be affected by exposure to ethylene oxide.

A need exists for a biological indicator which will evaluate or indicate the effectiveness of a sterilization process in a very short period of time. Preferably such a biological indicator should be a direct measure of, or correlate with, the loss of spore or cell viability. The capability to rapidly assess the effectiveness of a sterilization process will allow users of such sterilization processes to work more efficiently and with a greater degree of reliability.

SUMMARY OF THE INVENTION

The present invention provides a novel method of assessing or determining the effectiveness of a sterilization process. According to this invention, the method includes the steps of i) contacting an indicator comprising microbial spores with a sterilant to give exposed spores, ii) contacting the exposed spores with a medium selected to germinate the spores, iii) determining a rate of germination of the exposed spores in order to assess or determine the effectiveness of the sterilization process.

The present method may be employed with a variety of sterilization apparatus and techniques that are typically used. For example, this method may be used to monitor sterilization effectiveness of known sterilants or sterilization processes such as steam, ethylene oxide, radiation, heat, sodium hypochlorite, polyvinylpyrrolidone-iodine, sodium dichlorocyanurate, low temperature steam-formaldehyde, glutaraldehyde and hydrogen peroxide, hydrogen peroxide plasma or mixtures of these sterilants or processes.

In one preferred embodiment, this invention provides a method of determining the effectiveness of an ethylene oxide sterilization process. In this embodiment, bacterial spores of *Bacillus subtilis* ATCC accession number 9372 are included with a load exposed or subjected to ethylene oxide sterilization following common practices. After this exposure, the spores are incubated at about 37° C. in a medium selected to enhance germination of the exposed spores. After a lag time of a few minutes, a linear reaction velocity (LRV) which provides a measure of a maximum declining portion on a reaction curve (in this case the LRV is the maximum germination rate for a selected sample) is calculated after an incubation time of about 4–20 minutes, preferably 5–7 minutes, at a temperature in the range of about 20°–45° C., preferably in the range of about 37°–40° C.

In this embodiment of the present invention, a LRV is determined by dividing a measurement of a change in the optical density of the exposed spores in the medium (absorbance at about 480 nanometers (nm) wavelength of light, ABS or abs.) by the change in time between such measurements (minutes). Linear reaction velocities correlate with the survival of viable spores or cells in a linear relationship. Briefly, the lower the LRVs, the lower the probability of non-sterile units (PNSU) in a given biological load which is subjected to a sterilization process.

Linear reaction velocities may be readily determined using known light scattering techniques by passing light through exposed spores suspended in germination medium in suitable transparent containers. For example, spore germination rates may be determined using both absorbance spectrophotometers (based on light absorbance) or nephelometers (based on light scattering) in view of the light scattering behavior of suspended spores. Alternatively, the medium may also include known indicators which produce detectable responses in the presence of germinating spores and a measurement of a change in the indicator caused by spore germination is then used to determine a LRV. Suitable indicators include tetrazolium salts such as 2,3,5-triphenyltetrazolium chloride, nitroblue tetrazolium, 2-(p-iodophenyl)-3-(p-nitrophenyl)-5-phenyl tetrazolium chloride, cyanoditolyl tetrazolium chloride or other redox dyes or indicators which are used to assay or measure microbial enzymatic activity.

In another embodiment, the present invention provides a biological indicator system to determine the effectiveness of a sterilization process. A preferred system includes container means adapted to retain microbial spores in a vessel that will allow the microbial spores to be exposed to a sterilant as well as allowing the exposed spores to contact a germination medium, germination means adapted to contact the spores with a medium and incubate the spores, and detection means adapted to measure the germination rate of incubated spores, calculate a LRV for the exposed, incubated spores and provide an indication of the effectiveness of a sterilization cycle from the calculated LRV.

One preferred biological system includes bacterial spores of *Bacillus subtilis* ATCC accession number 9372 contained in transparent poly(methyl methacrylate) cuvettes, germination medium containing nutrients, ions and a germinant, and an absorbance spectrophotometer equipped with temperature control and computor capabilities for recording and calculating LRVs.

DETAILED DESCRIPTION

Figure 1:
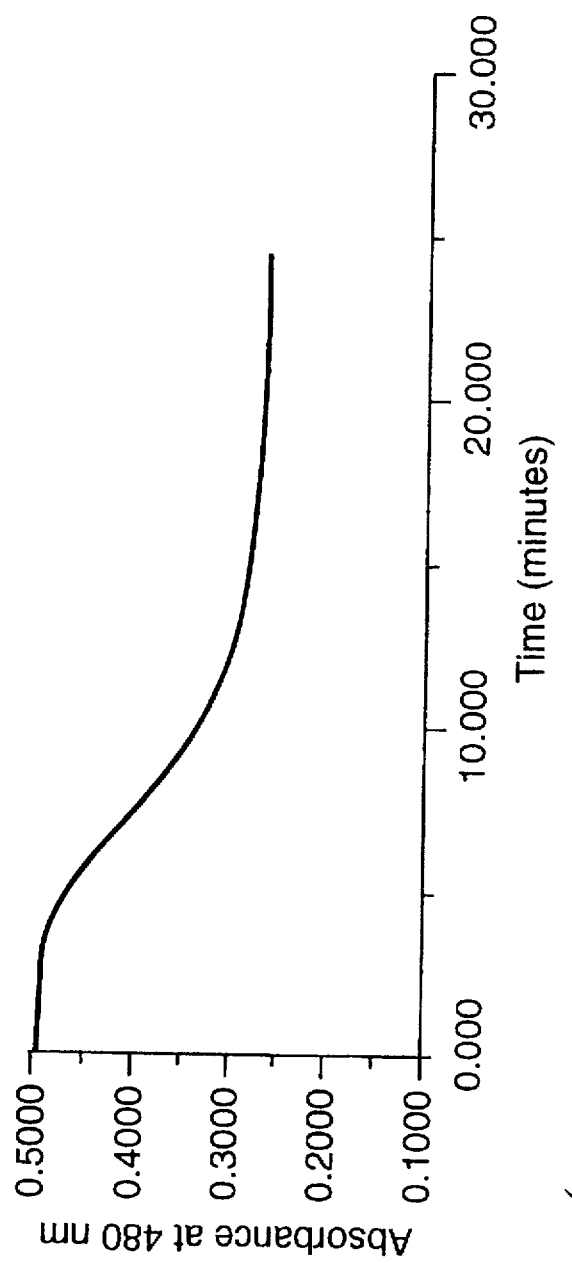
FIGS. 1 and 2 are graphical representations of measured germination rates or germination kinetics of *Bacillus subtilis* spores and *Bacillus stearothermophilus* spores, respectively.
Figure 2:
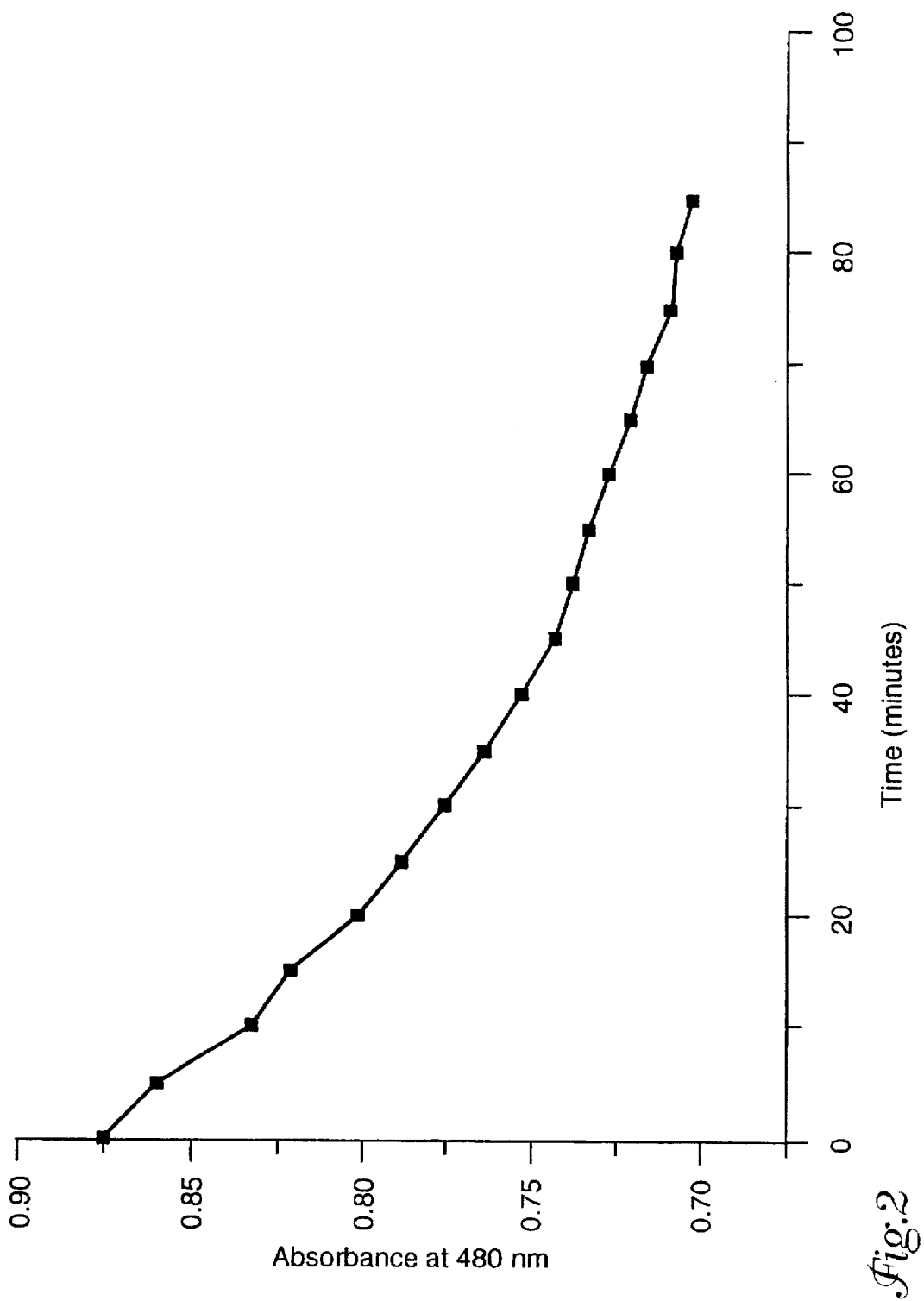

The present specification describes a very rapid method of assessing or determining the effectiveness of a sterilization process. This invention exploits the observation that spore germination is extremely sensitive to a sterilizing environment and that a measurement of a rate of spore germination may be directly correlated with cell viability or spore survival after exposure to a sterilant or sterilizing process. In other words, a measurement of the rate of spore germination correlates with the kill curves of viable microbes associated with a bioburden of a sample which is subjected to sterilization processes.

Both growth based and enzyme based biological indicators (BIs) referred to above are effective only if one or more viable spores survive per unit and grow out to form a population of cells large enough to detect. To detect lower levels of survival in a given load, the number of BIs assayed must be increased. For example, at least 458 BIs would be needed to detect a survival level or sterilization endpoint of 0.01 viable microorganisms per unit. Such a large number of BIs is impractical to use in order to monitor sterilization processes. Consequently, current BIs do not indicate that a desired sterilization endpoint, such as $10^{-6}$ microorganisms per unit, is reached during a sterilization process. Rather, such BIs indicate, if the assay result is positive, that one or more viable spores survived per unit. Thus, there is a need for a BI that can provide a numerical value for sterilization endpoint PNSUs of $10^{-6}$ microorganisms or less.

In particular, the rate of spore germination, within minutes after being incubated with a germination medium containing selected germinants, allows a prediction of the number of viable surviving spores. Simply put, the sensitivity of the germination process and the direct relationship of germination rate to viability allows use of a rate of germination of bacterial spores to provide a very rapid indication of the effectiveness of a sterilization process to sterilization endpoints of the PNSU of $10^{-6}$ and even lower PNSUs.

In one aspect of the present invention, germination rates or germination kinetics may be obtained using bacterial spores contacted with a germination medium which contains specific germinants. Although it is possible to measure or obtain germination rates or kinetics using light scattering techniques over a wide range of wavelengths of light, it was found that the germination rates were fastest and most reproducible at wavelengths of about 460–520 nanometers (nm) at an optimal temperature in the range of about 37°–40° C. Furthermore, for a given concentration of spores, the light absorbance drops asymptotically between 400–700 nm. Thus, below 480 nm the absorbance begins to rise steeply, and above 480 nm it declines gradually, requiring, in part, use of higher concentrations of spores at those wavelengths greater than 480 nm.

The maximum germination rate or LRV (the maximum declining portion of the reaction curve) of the exposed spores may be readily determined using spectrophotometric or light scattering techniques with or without staining of germinated spores using apparatus and processes known in the art. The LRV of a particular sample is readily calculated by dividing the change in the absorbance of light or the light scattering in a sample by the change in time. When absorbance is used to measure the optical density, which provides a measurement of the number of germinating spores in solution, the LRV for a particular sample is given by the formula.

LRV=change in light absorbance units/change in time in minutes

The absorbance may be readily calculated at commonly used wavelengths of light, about 400–600 nm and preferably about 480 nm. Preferred time periods between absorbance measurements are about 4–20 minutes or, most preferably, about 5–7 minutes.

It has been observed that death of microorganisms within a population due to an external factor, such as an ethylene oxide sterilant (ETO), is described best using first order kinetics, since the decrease in the number of such organisms is logarithmic. See, for example, Pflug, I. J. and R. G. Holcomb, "Principles of the thermal destruction of microorganisms", *Disinfection, Sterilization, and Preservation*, Fourth Edition, S. S. Block, ed., Lea and Febiger, (1991). Thus, the number of organisms surviving per unit after increasingly longer exposure to a sterilization or killing treatment such as ETO may be determined using the following linear regression equation and then plotting the calculated data on semilog graph paper.

$$\log N = -U/D + \log N_o$$

where N is equal to the number of microorganisms remaining per unit after ETO exposure for a given time, U. U is equal to the number of minutes of ETO exposure. D is a decimal reduction time (specifically, minutes required to kill one log of spores or cells) which is a constant for a given set of conditions and a given batch or crop of spores or cells. Thus, D is the negative reciprocal of the slope of a straight-line death curve. $N_o$ is equal to the number of spores or cells per unit at the beginning of the sterilization process.

Figure 3:
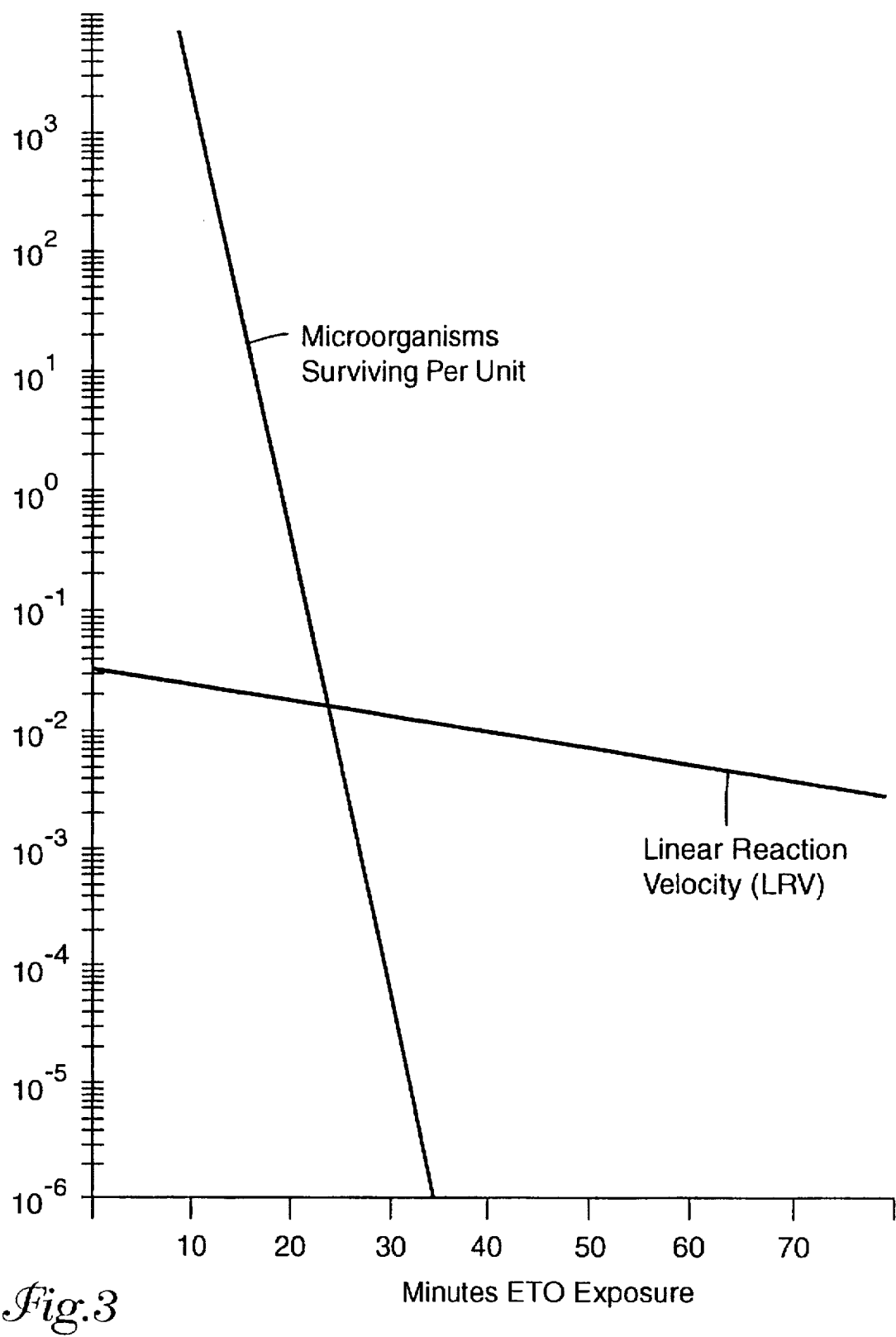
FIG. 3 is a graphical representation of a survival curve for *Bacillus subtilis* spores exposed to ethylene oxide having a D value of 2.7 minutes and an observed LRV curve for this type of bacterial spore.
Figure 4:
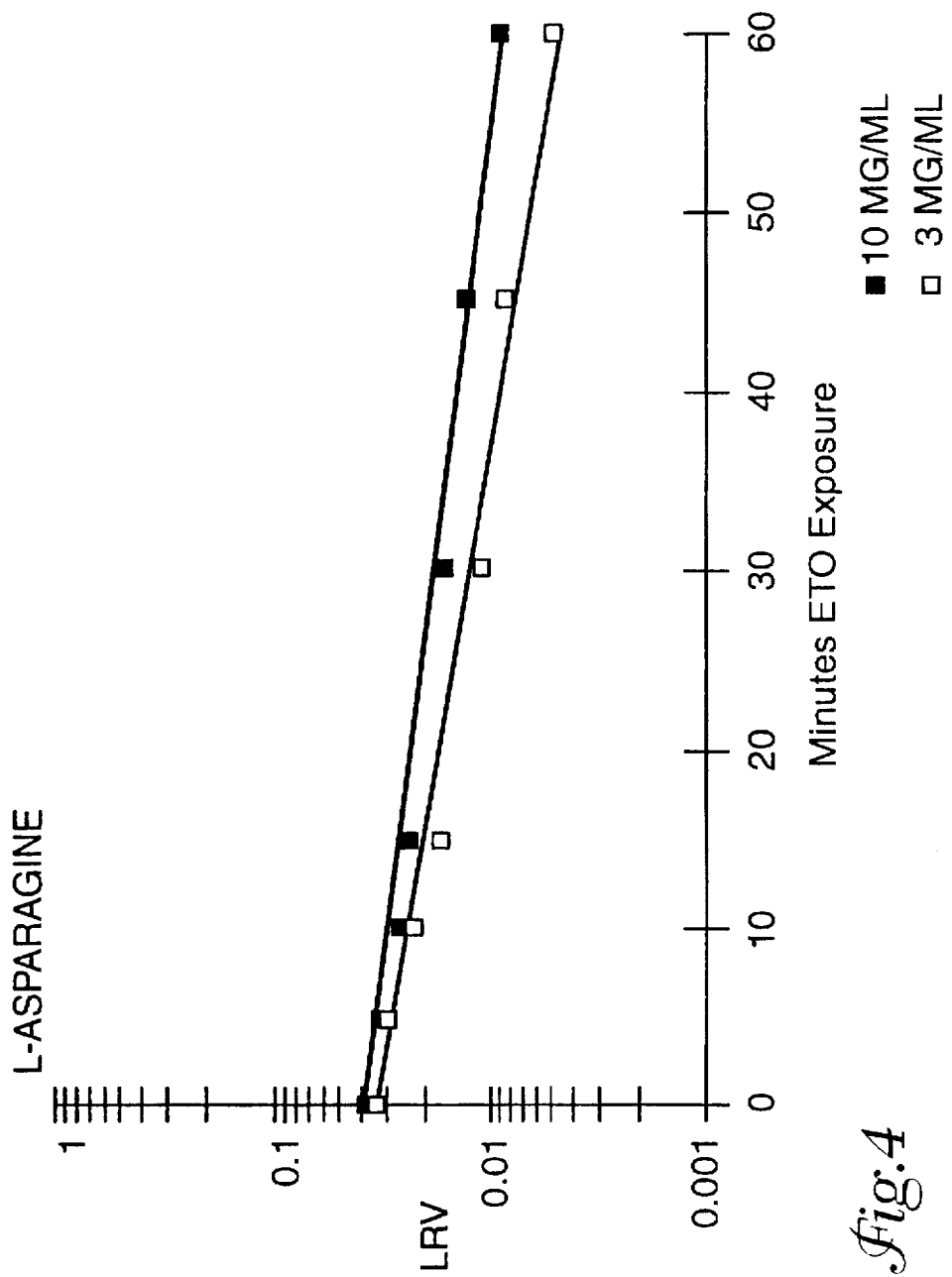
FIGS. 4–10 are graphical representations of the linear reaction rates of *Bacillus subtilis* spores in different media or in the presence of different germinants after the spores are exposed to ethylene oxide.
Figure 5:
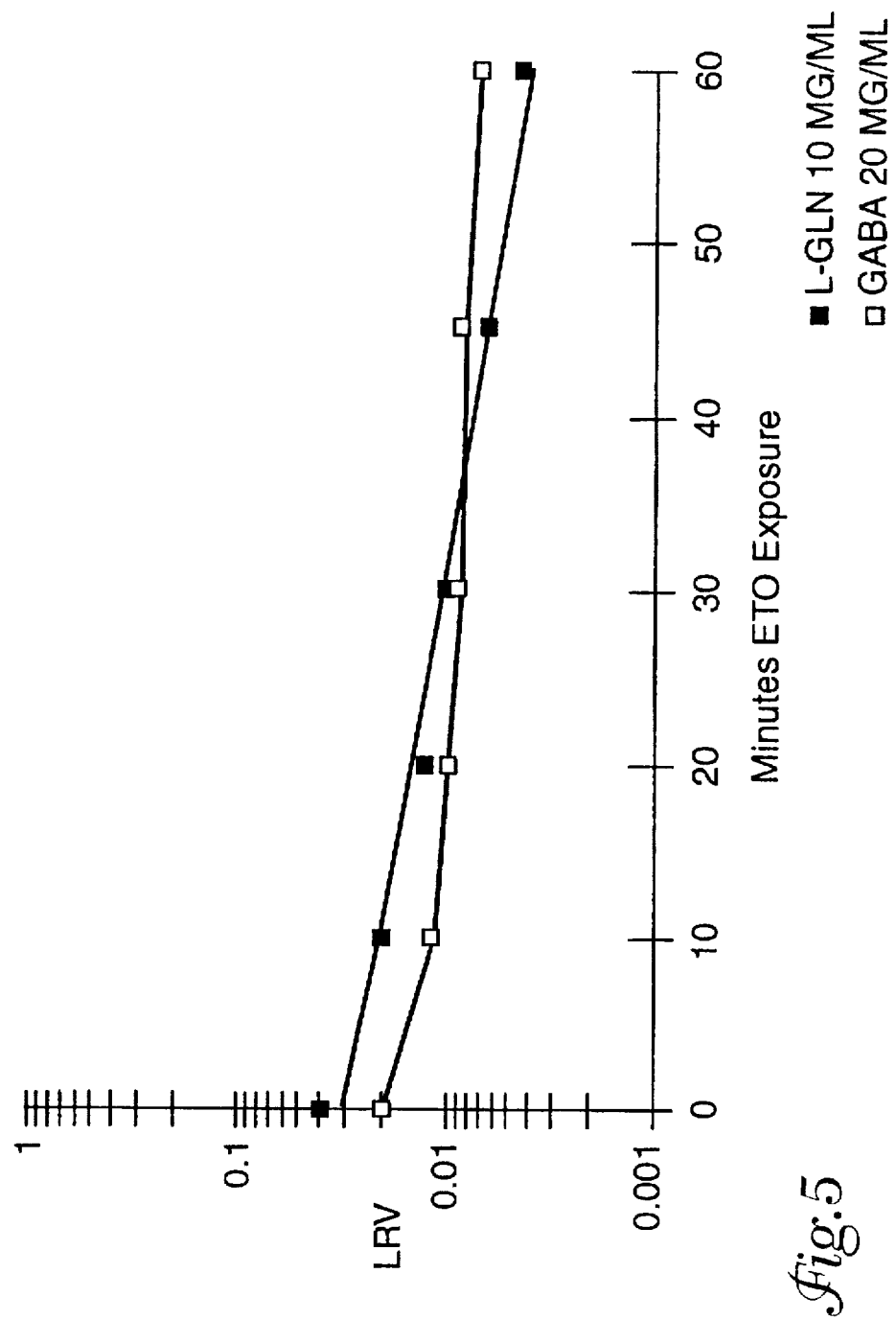
Figure 6:
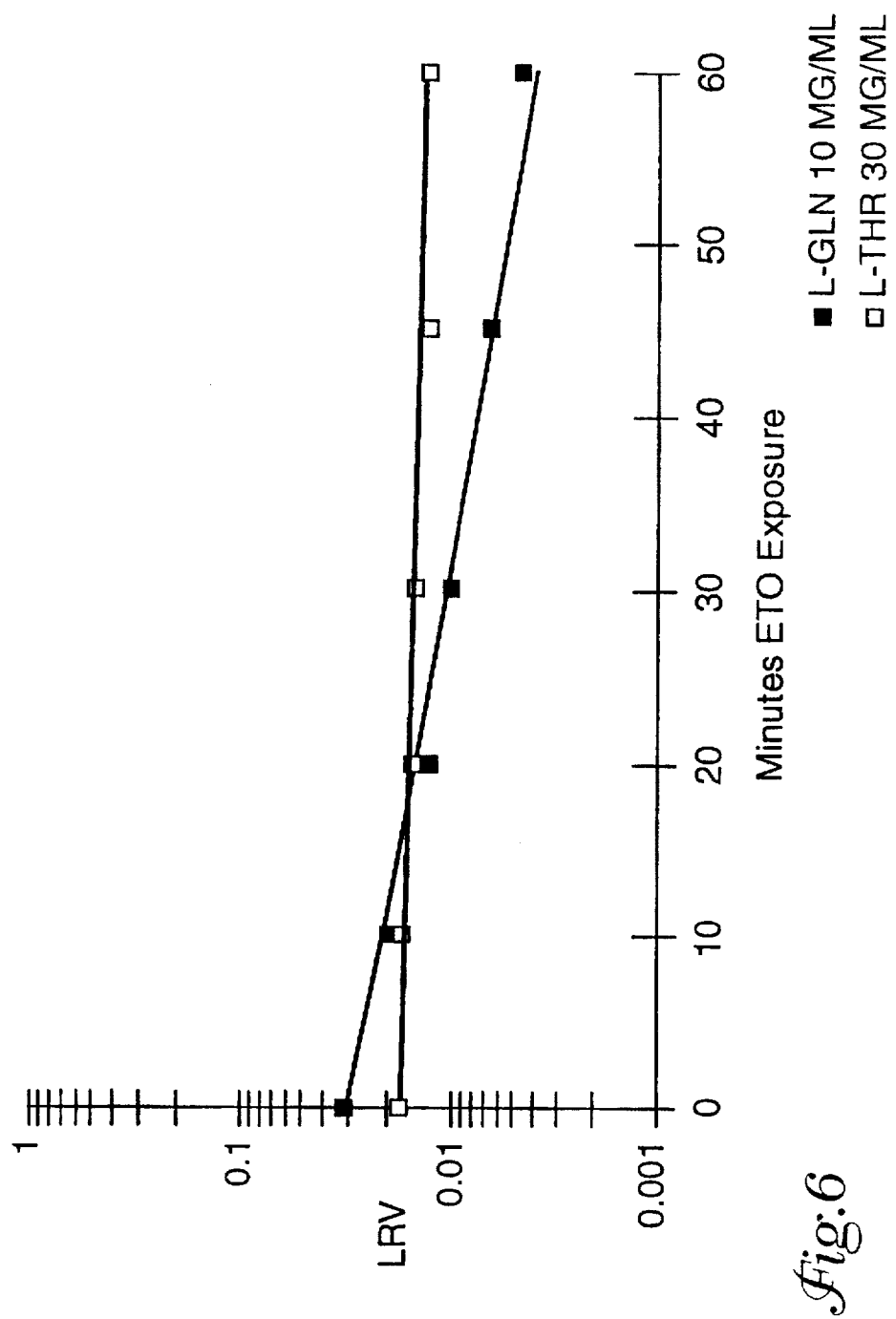
Figure 7:
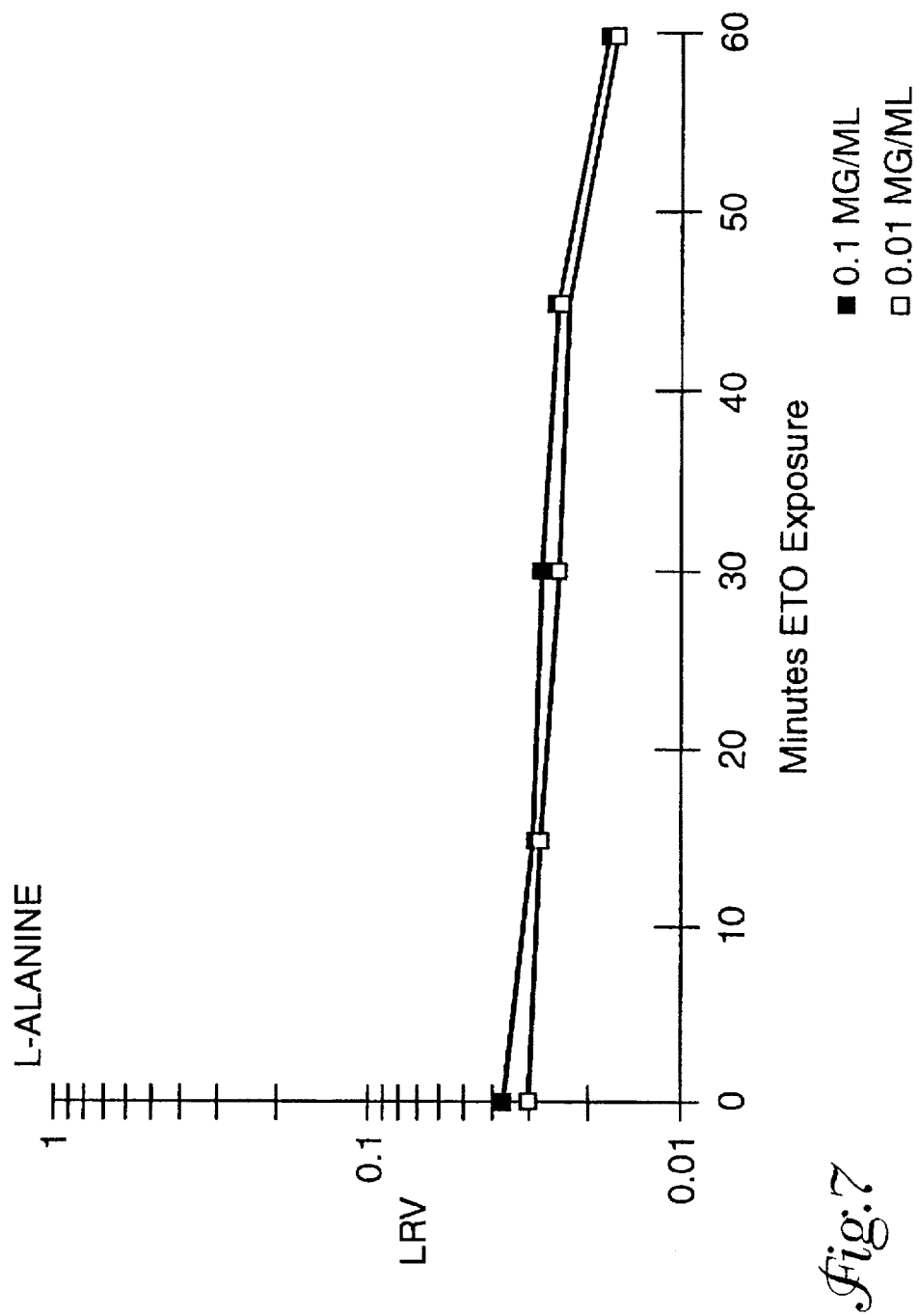
Figure 8:
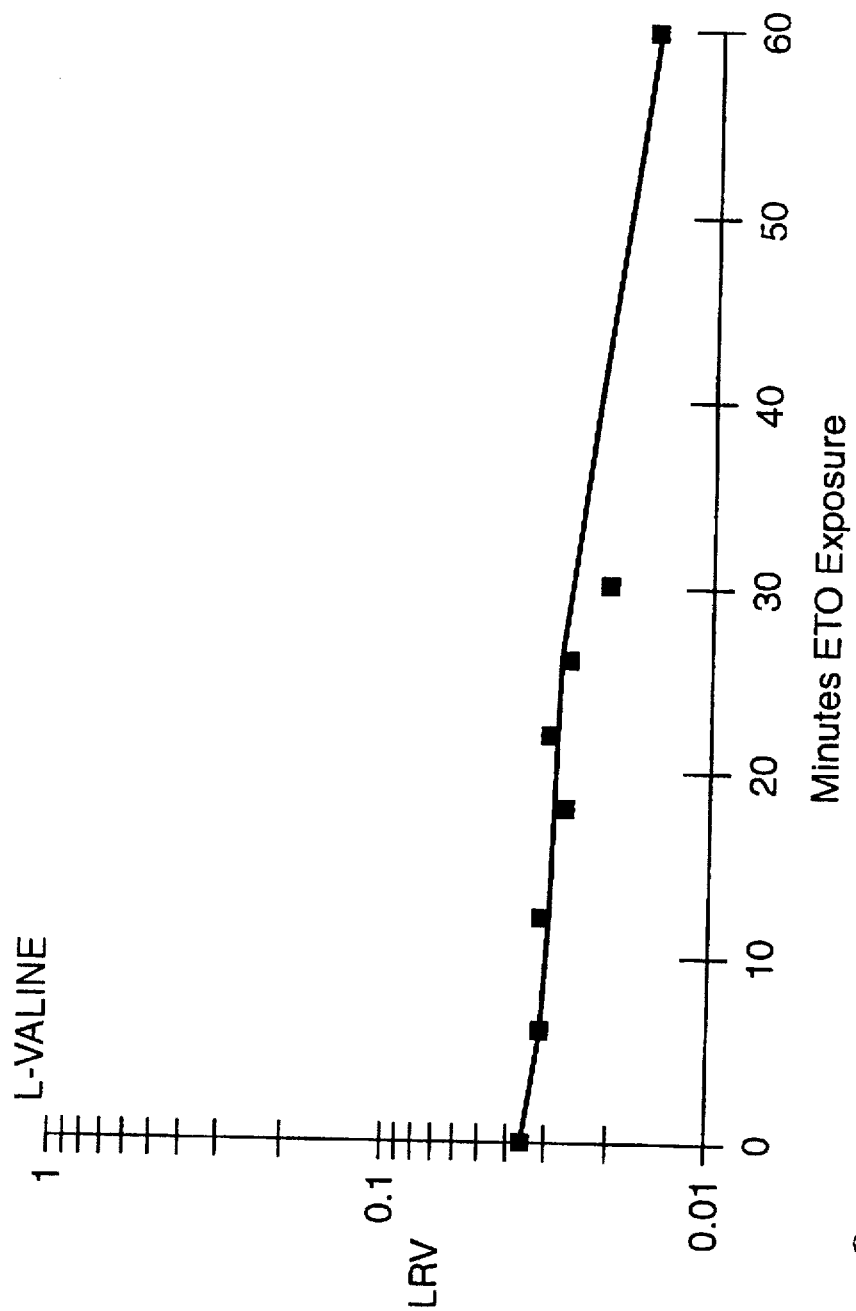
Figure 9:
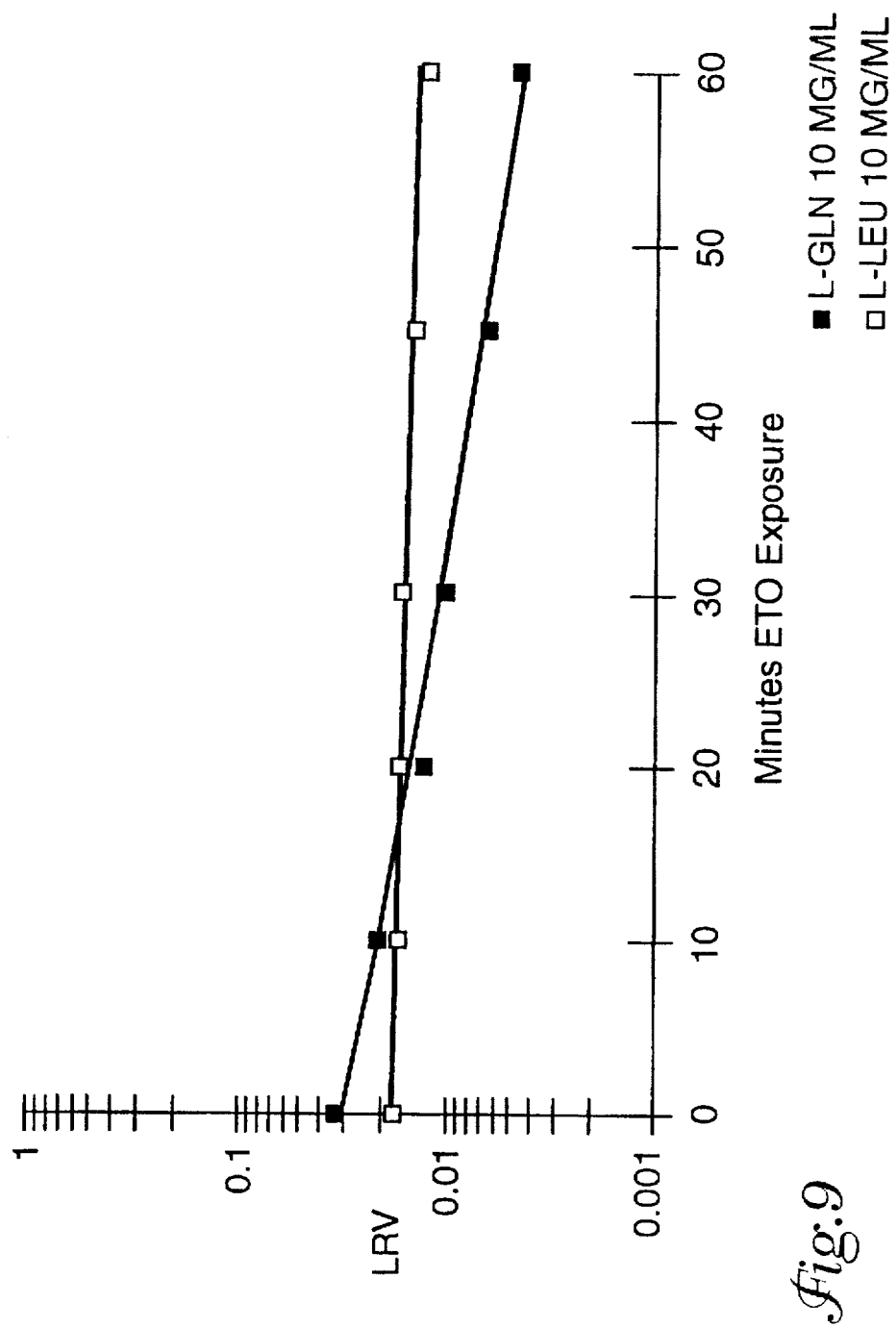

FIG. 3 illustrates that the linearity of the LRV response curve to the duration of ETO exposure and the correlation of the experimentally determined LRV data and the calculated survivor curve of *B. subtilis* spores. For the data shown in FIG. 3, the D value was determined to be 2.7 minutes and the $N_o$ value was $4.2 \times 10^6$ spores per unit ( 3M 1264 ATTEST Biological Indicator, lot #211, 3M, St. Paul, Minn.). With different D values, the slope of the survivor curve changes. As a result, LRVs of the surviving *B. subtilis* spores after exposure to sterilization conditions, such as gas, correlate with the survival of cells of any organism that could possibly be found in the bioburden of the load or materials being sterilized. Using the present LRV approach of assaying spore survival after a sterilization process thus makes it possible, for the first time in the use of biological indicators, to obtain a direct quantitative measure of the expected survival of any microorganism from the least resistant to the most resistant. Furthermore, using the LRV approach it becomes possible to assess the degree of sterilization effectiveness at levels at least as low as $10^{-16}$ viable microorganisms remaining per unit.

In a preferred embodiment of this invention a load including a biological indicator containing bacterial spores is contacted with a sterilant to give exposed spores. Suitable spores which may be used in this invention include spores which are commonly used to monitor sterilization processes such as steam, dry heat, gamma irradiation and ethylene oxide. Preferred spores include spores of both Bacillus and Clostridia species. Other suitable microbial spores for use in biological indicators are listed in U.S. Pat. No. 3,661,717. *Bacillus subtilis* spores, such as commercially available *Bacillus subtilis* spores ATCC 9372 (American Tissue Culture Collection, Rockville, Md.) are preferred for monitoring processes using ethylene oxide while *Bacillus stearothermophilus* spores, such as commercially available *Bacillus stearothermophilus* spores ATCC 8005 or ATCC 7953 (American Tissue Culture Collection) or *Bacillus stearothermophilus* spores DV 296 (obtained from the culture collection of the School of Pharmacy and Pharmacology, University of Bath, Bath, U.K.) are preferred for monitoring processes using steam or low temperature steam formaldehyde sterilization. If desired, other microorganisms which are suitably resistant to sterilization process may be used in this invention. If desired, one or more types of spores may be used in combination in the present process in order to monitor more than one type of sterilization process.

To practice this invention, selected spores are preferably prepared according to known methods and then a calibrated number of spores is added to a container or vessel preferably adapted to retain the spores in the container or the vessel during and after the sterilization process. The spores are generally added as an aqueous suspension to a container and then dried or dried before being added to the container. Spores may be dried in several different known ways as well as being dried in the presence of water soluble gels or other agents that facilitate resuspension of dried spores in a germination medium after the spores have been exposed to a sterilization process. See, e.g., Hanlon et al., *Letters in Applied Microbiology*, 17:171–173 (1993) that reports using spores incorporated into lyophilized alginate beads for use in biological indicators.

Containers adapted to retain suitable spores may be of a variety of shapes and made from a variety of known materials. Suitable containers will allow access of a sterilant to the spores in the container. In addition, if the germination rate is to be determined spectrophotometrically, a suitable container which is transparent to selected frequencies of light and which will not interfere with such detection processes is preferred. Finally, a suitable container preferably prevents the spores from becoming contaminated before and/or during the germination period. Those of ordinary skill in the art would recognize that a variety of container shapes made from quartz glass or a variety of polymeric materials, such as poly(methylmethacrylate) or polystyrene, may be used to practice this invention.

A preferred container allows contained spores to come into contact with a selected sterilant as well as a suitable germinating media. Dried spores can be resuspended in the germination medium in several different ways. Medium for spore germination can be added in several different ways either manually by syringe or pipette, or in an automated fashion as part of a process programmed in an autoreader apparatus specifically adapted and designed to handle and analyze results of sterilization monitoring using a spectrophotometric approach as described in the examples, below.

In order to obtain the extremely rapid read-out times of this invention, i.e., in less than about 10–15 minutes, the germinating medium is formulated to provide nutrients, ions and other components which promote rapid germination of exposed spores. The $K_M$ and $V_{max}$ of sixteen amino acids that were suitable as germinants of *B. subtilis* spores were determined from concentration/response curves in order to determine useful concentrations of these amino acids for use in medium to germinate ETO exposed spores. Three amino acids which were tested were not active as germinants at any concentration up to the limit of their respective solubilities. Of the most active amino acid germinants, ETO response curves were determined as described in Example 6 below. A linear decrease in LRV was obtained only with L-asparagine and L-glutamine. When spore germination was activated with the other tested amino acids there appeared to be very little effect of ETO since the LRV response decreased little or not at all. For example, there was a significant decrease in LRV response activated by L-alanine and L-valine only after about 40 minutes of exposure to ETO. Thus, it was found that L-asparagine and L-glutamine were the most useful amino acid germinants for measuring the killing effect of ETO on *B. subtilis* spores.

Furthermore, it was observed that the D-amino acids appear to be competitive inhibitors of the binding of the L-amino acids to the sites responsible for triggering spore germination. See, for example, Woese, C. R.; Morowitz, H. J.; and Hutchinson III, C. A.; "Analysis of action of L-alanine analogues in spore germination", *J. Bacteriol.*, 76:578–588 (1958). One potent inhibitor of the L-amino acid germinants is D-alanine. In experiments measuring the competitive inhibition of spore germination in response to L-asparagine, the results indicated two binding sites for D-alanine and L-asparagine, one at concentrations of D-alanine from 0.3–10 microgram/ml and another at concentrations of D-alanine from 10–100 mg/ml. Since the effective concentrations for L-asparagine are in the range of 1–15 mg/ml, it appears that L-asparagine binds mostly to the low affinity site or sites. Hence, the low affinity binding site or sites for the L-amino acid germinants must be the site that is sensitive to ETO inactivation while the high affinity site or sites must be the site insensitive, or at least far less sensitive, to ETO inactivation. Consequently, by inhibiting the binding of L-asparagine to the high affinity site with D-alanine at very low concentrations, it was possible to eliminate the contribution of the ETO insensitive germination system to the spore germination response. LRV, activated with L-asparagine and thus obtain a desired steeper LRV response curve.

A preferred medium for this invention when Bacillus spores are used includes the following components, 0.01–0.2M, preferably 0.05 M, phosphate buffer (equal parts $KH_2PO_4$ and $Na_2HPO_4$), 0.15 g glucose per liter, 0.15 g fructose per liter, 3.0 g NaCl per liter, 5.0 g potassium acetate per liter, and 3–15 g, preferably 10 g, L-asparagine per liter at a pH in the range of about 6.8–7.8 and preferably about 7.25. Alternatively, L-glutamine may be used as a germinant, at a concentration of about 10.0–20.0 g per liter and prefereable in a concentration of about 10.0 g per liter.

It has been observed that the germination rate of Bacillus spores is sensitive to the sterilization environment, to the handling conditions of the spores, and to the germinating medium. In particular, it has also been observed that small changes in humidity or in a germination medium may have an observable effect on spore germination. It has also been observed that there is a brief lag period before the germination rate becomes linear. This lag period is typically very short but is related to the handling and sterilization environments of the exposed spores. For example, when spores are dried at about 37° C., this lag period is about 8–9 minutes as compared to a lag period of about 4.5–5 minutes when the spores are dried at about 45°–55° C. After the initial lag period, however, the LRVs are readily determined in a time period of less than about 10 minutes.

When the sterilant is ethylene oxide and the bacterial spores are spores of *Bacillus subtilis* ATCC accession number 9372, the present method indicates that a sterilization process is effective when the calculated LRV for a particular spore sample containing about $10^8$ spores per cuvette is equivalent to the expected sterilization endpoint of the most resistant microorganism expected in the bioburden of the load being sterilized. Thus, in the case of *Bacillus subtilis* spores having a D value of 2.7 minutes, as shown in FIG. 3, a linear reaction velocity of 0.01 absorbence units/minute would indicate that a sterilization endpoint with a PNSU of $10^{-6}$ was reached. Higher LRVs would be indicative of lower sterilization effectiveness, and lower LRVs would be indicative of greater sterilization effectiveness.

The present method is applicable for a range of known sterilants including but not limited to steam, ethylene oxide, radiation, heat, sodium hypochlorite, polyvinylpyrrolidene-iodine, sodium dichlorocyanurate, low temperature steam-formaldehyde, glutaraldehyde and hydrogen peroxide, hydrogen peroxide plasma or mixtures thereof. The results provided in the examples listed below indicate that the determination of linear reaction velocities is a very sensitive and very rapid measure of spore survival. It is faster than any biological indicators which are known or currently on the market and it is expected that the use of the present biological indicator system and process of this invention will be used to rapidly, in less than about 15 minutes, evaluate the effectiveness of a variety of processes such as steam, heat, and chemical sterilization and combinations thereof (such as low temperature steam-formaldehyde and hydrogen peroxide plasma sterilization).

The following examples are provided to further illustrate the practice of this invention. These examples should not be construed to limit the scope of this invention which is defined in the appended claims.

EXAMPLES

Example 1

Spore Germination Conditions

Spores of *Bacillus subtilis*, ATCC 9372, were used at a concentration of about $2 \times 10^8$ spores per 2 ml of medium contained in a clear poly(methyl methacrylate) cuvette. This concentration of spores gave an initial absorbance at 480 nm of about 0.4500 optical density (OD) units using a Cary 13/Varian spectrophotometer described below. Spore concentrations in the range of $1.5 \times 10^8$ to $6 \times 10^8$ spores per 2 ml were useful.

The standard germination (SG) medium contained 0.05M phosphate buffer made from $KH_2PO_4$ and $Na_2HPO_4$, each at 3.475 g per liter, and a pH of 7.0 at 22° C.; 0.1M NaCl; 5 g glucose per liter and 10 g L-asparagine per liter.

A Cary 13/Varian spectrophotometer, equipped with a temperature-controlled cuvette holder, was used to determine the germination kinetics by measuring absorbance. Germination kinetics may be measured at any wavelength of light in the range of 400–600 nm. It is preferred to use wavelengths in the visible range. The germination kinetics were determined at 37° C.

The LRV, a measure of the maximum germination rate for each selected spore sample, was determined from the linear portion of a calculated germination curve. The LRV was generally obtained from the negative slope of the germination curve in the interval of 4–10 minutes from the time the germination reaction was started. The highest LRVs were obtained in the interval of 4.5–6.5 minutes when L-alanine was the germinant in the medium, and in the interval of 5–7 minutes when L-asparagine was used as the germinant in the medium. When L-alanine was used as the germinant its preferred concentration was 0.4 g/L.

Example 2

Correlation of LRVs and Spore Survival After Exposure to ETO

Aliquots of about fourteen microliters of *Bacillus subtilis*, ATCC 9372, spore suspension were added to poly(methyl methacrylate) cuvettes delivering about $2 \times 10^8$ spores per cuvette. The spore aliquots were dried overnight (16 hours) at 54° C. Sets of cuvettes containing the dried spores and the 3M 1264 ATTEST biological indicator devices, (1264 BI devices as generally described in U.S. Pat. No. 3,661,717 and commercially available from 3M, St. Paul, Minn.) were placed inside a Joslyn-B.I.E.R. ETO vessel and exposed for various times to ETO. The ETO exposure cycles consisted of 30 minutes prehumidification at 54° C. and a relative humidity of 60%, followed by ETO release at a concentration of 600 mg per liter of air, and ending with a one minute aeration after the ETO was evacuated.

Following ETO exposure, the growth medium in the ampoules inside the 1264 BI devices was released by crushing the vials, and the devices were placed in an incubator at 37° C. to allow outgrowth of surviving spores over a seven day period. There were 160 1264 BI devices used at each ETO exposure time. Each device contained a spore strip with $5.4 \times 10^6$ spores.

Germination kinetics were determined for the cuvette spores exposed to ETO as follows. One milliliter of the SG medium described in Example 1, but without the germinant, was added into each cuvette and the spores were resuspended by shaking. Then a stir bar was dropped inside the cuvette and the cuvette was placed inside the temperature controlled cuvette holder in the spectrophotometer for 10 minutes of stirring at 37° C. to complete the resuspension of the spores (spores can also be resuspended in 2 milliliters of complete SG medium by vigorous shaking for one minute on a Vortex mixer, as was done in subsequent experiments). Next, one milliliter of SG medium containing 20 mg of L-asparagine was added into the cuvette, the germination kinetics were recorded and the LRVs were calculated in the spectrophotometer by dividing the change in measured absorbance at 480 nm by the change in time. The LRV for each ETO exposure was determined in the interval of 4.5–6.5 minutes. The results shown in Table I were obtained. The LRVs are averages of four replications.

TABLE I

| Minutes ETO Exposure | LRV OD units/min. | % St. Dev. | Spore Growth % Positive BI's |
|---|---|---|---|
| 0 | 0.0299 | 10.0 | 100.0* |
| 10 | 0.0185 | 4.2 | 100.0* |
| 20 | 0.0106 | 5.6 | 94.0 |
| 30 | 0.0065 | 4.6 | 0.0 |
| 40 | 0.0047 | 6.4 | 0.0 |
| 60 | 0.0031 | 11.3 | 0.0 |

*Expected, not tested in this experiment

These results indicate that a correlation exists between the LRVs and the percent of commercially available 1264 BI devices showing growth and thus survival of spores, i.e., the LRVs are directly proportional to the percentage of 1264 BI devices showing a positive color change due to outgrowth of surviving spores. To get the best correlation results, it is essential that the cuvettes with the dried spores be placed adjacent to the 1264 BI devices in the load in a sterilizer during the sterilization process. In this example under the listed conditions, an LRV of 0.005 abs./minute or lower was indicative of complete sterilization. An LRV of 0.005 to 0.008 abs./minute was indicative of marginal sterilization. An LRV greater than 0.008 abs./minute was indicative of complete sterilization failure.

Furthermore, these results indicated that the viability of the spore core cell, i.e., its ability to grow out and multiply, is much more sensitive to ETO than germination.

Example 3

Correlation of LRVs and Spore Survival After Exposure to ETO

The procedures were the same as in Example 1 above, except that the spores in the cuvettes were dried overnight (16 hours) at 37° C. and that the spores were resuspended in the cuvette after adding two milliliters of complete SG medium by mixing vigorously for one minute on a Vortex mixer. The LRV for each ETO exposure was determined from the germination curve in the interval of 5–7 minutes to compensate for the slightly longer lag before germination when the dry spores were resuspended by mixing on a Vortex mixer. The LRV of the germination of spores not exposed to ETO (0 min. ETO) was determined in the 8–11 minute interval of the germination curve because there was a longer lag period before germination of spores that were dried at 37° C. instead of 55° C. Germination of spores exposed to ETO did not have such a long lag period because they were exposed to the higher temperature during the ETO sterilization process in the Joslyn-B.I.E.R. vessel. This temperature effect on spore germination is a well-known phenomenon.

TABLE II

| Minutes ETO Exposure | LRV OD units/min. | % St. Dev. | Spore Growth % Positive BI's |
|---|---|---|---|
| 0 | 0.0241 | 3.3 | 100.0* |
| 10 | 0.0115 | 6.1 | 100.0* |
| 20 | 0.0078 | 7.7 | 99.4 |
| 25 | 0.0105 | 7.6 | 55.0 |
| 30 | 0.0057 | 10.6 | 0.0 |
| 60 | 0.0021 | 14.3 | 0.0* |

*Expected, not tested in this experiment

The results in this experiment were essentially the same as in the previous one, i.e., the LRVs were directly proportional to the percentage of BI's showing a positive color change due to outgrowth of surviving spores after exposure to ETO.

The lower LRVs in this experiment were due to the method of drying the spores and not due to the method of resuspending the spores in the cuvettes prior to the spectrophotometric measurements. Spores dried at 37° C. are expected to retain more moisture than spores dried at 55° C., and it is well-known in the art of spore sterilization with ETO that spore death rate is directly proportional to the moisture content of the spores.

Spores exposed to 25 minutes of ETO sterilization showed a higher LRV of germination than expected. This departure from the linear relationship between LRVs and spore survival seen in all other experiments most likely was due to a tighter fitting aluminum foil cover over the cuvettes during the sterilization process. Thus, the dry spores in the cuvettes were exposed to a lower level of ETO than was desired. Nevertheless, even with this excursion from the norm, the correlation between LRVs as determined here and the survival of spores of *Bacillus subtilis* exposed to ETO still held true.

Example 4

Correlation of LRVs and Survival of Viable Spores After Exposure to ETO

The procedures were essentially the same as in Examples 1–3 above, except for the following changes. Spores of *B. subtilis* suspended in deionized water at concentrations of about $7.5 \times 10^9$ ml were conditioned by heating the suspensions for 2–6 hours, preferably for 4 hours, so as to obtain maximum germination rates. To reduce the number of spores per cuvette but still retain the starting optical density (OD) in a preferred measured range of about 0.45–0.5 units, semimicro poly(methyl methacrylate) cuvettes were used. About 16 microliters of the conditioned spore suspension were added to each cuvette so as to give a starting OD of about 0.45–0.5 when resuspended in 1.2 ml of germination medium. The cuvettes with the wet spores were then placed in an incubator and dried overnight (about 16 hours) at 45°–50° C., the empirically determined optimal temperature range for maximum germination rates of these spores. After this overnight drying, the spores may be stored at room temperature without lose of germination activity. Four such cuvettes were used per exposure/treatment.

Cuvettes with spores and the 3M 1264 ATTEST biological indicator (BI) devices ( batch 263, D=2.7 min., $4.8 \times 10^6$ spores/BI) were exposed to ETO in the Joslyn-B.I.E.R. vessel as described in previous examples except that a 15 minute preconditioning period at a temperature of 54° C. was added before the 30 minutes dwell at 60% relative humidity and before the cuvettes were subjected to the complete ETO exposure cycle. This preconditioning period was done to eliminate the variability in the response of the spores to the ETO. If a load in the vessel is not equilibrated to the appropriate temperature prior to the humidification step, the correct humidity levels may not be reached. Consequently, the sterilization effectiveness for a given ETO exposure time will vary depending on the size of the load. It appears that this was the most probable cause of the anomaly in Table II, above, at the 25 minute ETO exposure. After the ETO exposure cycle, the cuvettes and 1264 BI's were allowed to aerate at ambient temperature for 20–24 hours prior to initiating growth and determing germination rates.

Germination rates were determined essentially as previously described except that the spores were resuspended in 1.2 ml of germination medium by vortexing for 30–45 seconds in the Vortex Genie II set at maximum speed. No stir bar was placed in the cuvette after resuspending the spores since the spores stayed in suspension for the duration of the germination period. The germination medium was 0.05M phosphate buffer (equal parts $KH_2PO_4$ and $Na_2HPO_4$), 0.15 g glucose per liter, 0.15 g fructose per liter, 3.0 g NaCl per liter, 5.0 g potassium acetate per liter, and 10 g L-asparagine per liter. The pH was 7.25. The germination medium was sterilized by filtration through nylon membranes with 0.2 micrometer pore size. There were four replicates for each data point.

TABLE III

| Minutes ETO Exposure | LRV OD units/min. | % St. Dev. | Spore Survival % BI's Positive |
|---|---|---|---|
| 0 | 0.0301 | 2.8 | — |
| 5 | 0.0253 | 4.1 | — |
| 15 | 0.0187 | 3.8 | 100 |
| 20 | *0.0155 | 1.3 | 98.8 |
| 30 | 0.0120 | 2.2 | 0.6 |
| 45 | 0.0073 | 4.4 | 0.0 |
| 60 | 0.0048 | 10.5 | — |

*LRV derived from the linear ETO response curve.

The results indicate a direct correlation between the LRV and the percent survival of viable cells as determined by the BI devices. With the improvements in the procedures and the germination medium, as described in this example, the observed experimental variability in the linear reaction velocities was reduced to an average of 4.5% within a range of 1–11%. The variability in the percent viable survivors is somewhat greater because of the steepness of the survivor curve (see for example, FIG. 3).

Example 5
Correlation Between LRV and the Predicted Survival of Viable Spores

This data listed in Table IV below were generated using the linear regression equation explained in connection with FIG. 3. In this equation, $N_o$ was $4.2 \times 10^6$ spores per BI (lot 211, 3M 1264 Attest BI) and the D value was 2.7 minutes. The LRV values were taken from Table III in Example 4. The data illustrate that LRV determinations can be used to assess survival of viable spores in a large population during a sterilization process at survival frequencies far below what can be determined using common spore or cell growth biological indicators.

TABLE IV

| Minutes ETO Exposure | U/D | −U/D + log No | N (viable spores/unit) | LRV (Table 3) |
|---|---|---|---|---|
| 5 | 1.8518 | 4.7714 | $5.9 \times 10^4$ | 0.0253 |
| 10 | 3.7037 | 2.9195 | $8.3 \times 10^2$ | — |
| 15 | 5.5555 | 1.0677 | $1.2 \times 10^1$ | 0.0187 |
| 20 | 7.4074 | −0.7842 | $1.6 \times 10^{-1}$ | 0.0155 |
| 25 | 9.2593 | −2.6361 | $2.3 \times 10^{-3}$ | — |
| 30 | 11.1111 | −4.4879 | $3.3 \times 10^{-5}$ | 0.0120 |
| 35 | 12.9630 | −6.3398 | $4.6 \times 10^{-7}$ | — |
| 40 | 14.8148 | −8.1916 | $6.4 \times 10^{-9}$ | — |
| 45 | 16.6666 | −10.0434 | $9.1 \times 10^{-11}$ | 0.0073 |
| 50 | 18.5185 | −11.8953 | $1.3 \times 10^{-12}$ | — |
| 55 | 20.3704 | −13.7472 | $1.8 \times 10^{-14}$ | — |
| 60 | 22.2222 | −15.5990 | $2.5 \times 10^{-16}$ | 0.0048 |

The logarithmic nature of death of a population of microorganisms makes it impossible to reach absolute sterility. Thus, the generally acceptable sterility endpoint is a probability of non-sterile units (PNSU) of $10^{-6}$. This means that out of one million units being sterilized only one will be contaminated with a viable spore (Pflug, I. F., "Chapter 4—Description, establishment, and statistical characteristics of the endpoint of a microbial preservation process", *Microbiology and Engineering of Sterilization Processes*, Seventh Edition, Published by Environmental Sterilization Laboratory, Minneapolis, Minn. (1990)). It is impractical to determine survival of viable spores below a PNSU of $10^{-3}$ because, even at this sterility endpoint, one would need a minimum sample size of 4603 BI units ( Spicher, G., "Sterilization —Die Mikrobiologie zwischen Anspruch und Wirklichkeit," *Zbl. Hyg.*, 194: 223–235 (1993)). Moreover, as far as using BI's to monitor sterilization processes is concerned, it is impractical to use more than 100 BI's per load being sterilized, thus in effect limiting the sterility assurance to a PNSU of $10^{-1}$.

The consequence of this is that the current BI's, based on a readout of growth or on enzyme assays that merely indicate positive or negative results, do not indicate whether the required sterility endpoint, PNSU of $10^{-6}$, was actually achieved. With commonly used BI's, a positive result means that more than 0.1 viable spores survived per unit and thus the sterilization process was not effective. A negative result, however, merely indicates that fewer than 0.1 viable spores survived per unit.

The LRV approach makes it possible for the first time to assess whether the conditions during sterilization were such that the required sterility endpoint with a PNSU of $10^{-6}$, or lower, was reached. The LRV response is very sensitive to fluctuations in the conditions inside a sterilization vessel during the sterilization process.

Example 6
Response of Spores to Amino Acid Germinants After Exposure to ETO

Spores of *Bacillus subtilis* were exposed to ETO as explained in previous examples. Germination kinetics and LRV were determined as explained in Example 4. Abbreviations for some of the amino acids indicated in FIGS. 4–9 are as follows: L-GLN means L-glutamine; L-LEU means L-leucine; L-THR means L-threonine: GABA means gamma amino butyric acid; L-VAL means L-valine. Each data point is the average of four replications. The measured data graphically representing germination results using L-GLN were determined with spores that were exposed to ETO at the same time for each exposure time indicated.

These data indicate that, of the two postulated systems for spore germination believed to exist in B. subtilis spores, the system activated by L-ASN and L-GLN is sensitive to ETO while the other system activated by L-ALA (L-alanine) and other amino acids is not sensitive to ETO or is at least much less sensitive. Dadd and Rumbelow, J. Appl. Bacter., 60:425–433 (1986) speculated that the two germination systems, one activated by L-ALA and the other activated by L-ASN, might have different sensitivities to ETO although their data did not distinguish between the postulated two systems. The inability of Dadd and Rumbelow to distinguish the two spore germination systems, after exposure of spores to ETO, on the basis of their response to different germinants, was probably due to the fact that they were measuring the percent spore germination at two and more hours after the activation of spore germination by counting the number of phase dark (germinated) spores under a microscope but they did not measure spore germination rates. On the other hand, in the work reported here spore germination rates within the first 25 minutes after activation was the response measured. Furthermore, Dadd and Rumbelow claimed that L-LEU and L-THR failed to germinate ETO exposed spores. The results shown here clearly indicate that spores exposed to ETO do germinate in response to these amino acids. This again illustrates the unexpected results of the present invention.

Example 7

Effect of D-Alanine (D-ALA) on the LRV Response After Exposure of spores to ETO

The experimental procedures were the same as described in Example 4, except that, as indicated, D-ALA was added to the germination medium. Useful concentrations of D-ALA were 0.5–1.2 micrograms per ml of germination medium. The preferred concentrations of D-ALA were about 0.8–1.0 micrograms per ml.

Figure 10:
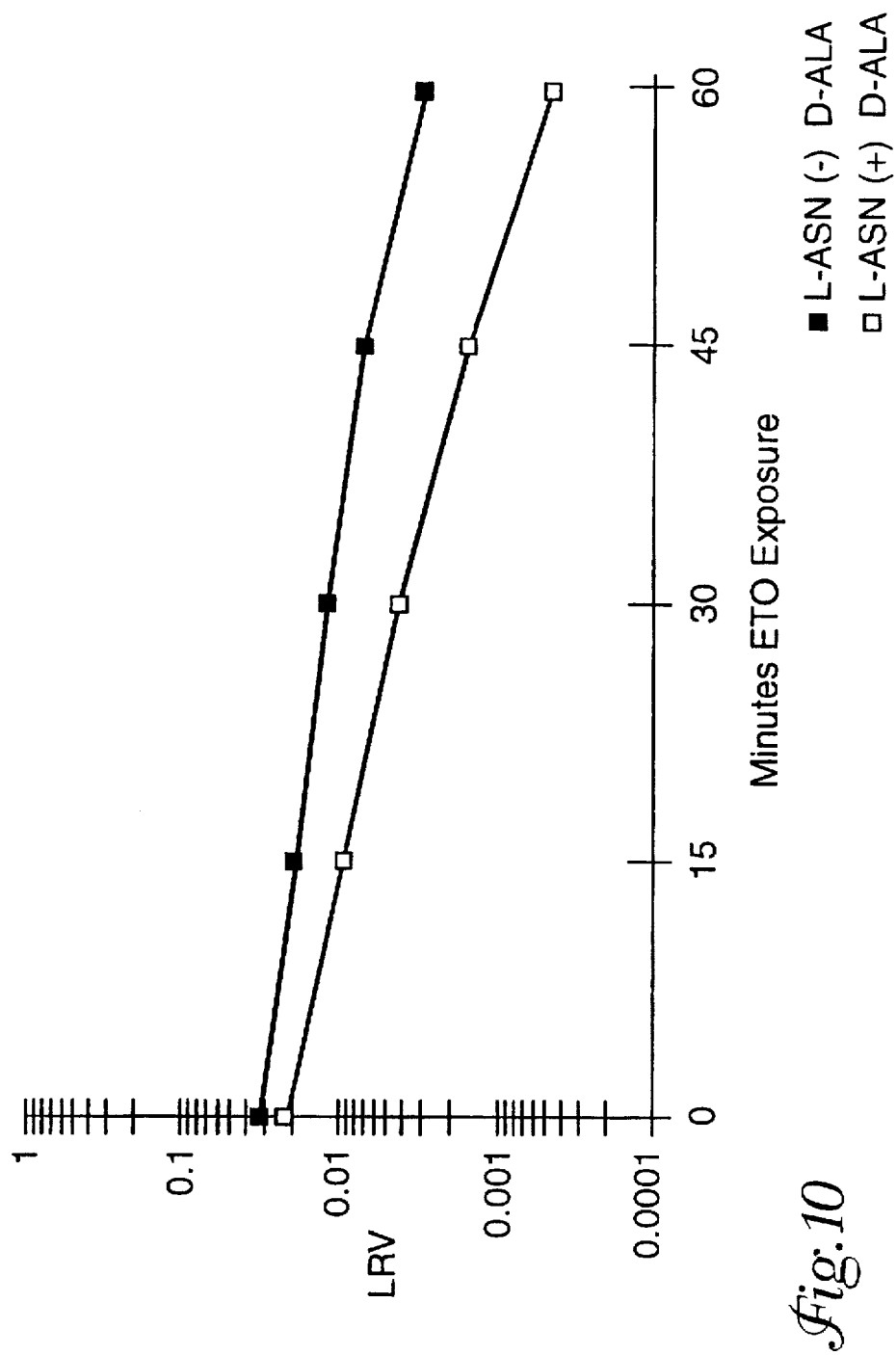

As illustrate in FIG. 10, addition of D-ALA at very low concentrations increased the slope of the LRV response curve by 26%, which in some circumstances might be desirable. Most probable explanation for this result is that, at low concentrations, D-ALA inhibits binding of L-ASN to the sites controlling activation of the germination system more or less insensitive to ETO. Thus, only the system which is sensitive to ETO was activated by L-ASN.

Furthermore, as shown in Example 6, these results indicate that most of the active amino acids probably bind to varying degrees to all the sites for all the germination systems (two or more) that seem to occur in B. subtilis spores. However, some amino acids such as L-LEU, L-THR and GABA bind, and thus activate, mostly the high affinity sites (in regard to binding of L-ALA and D-ALA), while others like L-ALA, L-VAL bind to the low affinity sites as well as to the high affinity sites. Thus, L-ALA and L-VAL have a steeper LRV curve in response to ETO than GABA, L-THR, or L-LEU, especially at longer exposures to ETO.

In some situations of sterilization, it may be desirable to have a steeper LRV response curve because of the greater sensitivity. Thus, addition of small amounts of D-ALA to the germination medium provides this desired result.

Example 8

Batch to Batch Variability in the LRV Response of B. subtilis Spores

The experimental procedures were the same as described in Example 4. The cuvettes with spores from the two different spore crops (batches) were exposed to ETO at the same time. There were four replications per data point. The germination medium was the same as described in Example 4.

TABLE V

| Minutes ETO Exposure | Batch 3/93 LRV | % Standard Deviation | Batch #26 LRV | % Standard Deviation |
|---|---|---|---|---|
| 0 | 0.0335 | 2.6 | 0.0307 | 5.8 |
| 2 | 0.0309 | 3.8 | 0.0279 | 4.7 |
| 15 | 0.0189 | 13.6 | 0.0197 | 5.2 |
| 40 | 0.0080 | 16.6 | 0.0062 | 10.6 |
| 60 | 0.0037 | 16.6 | 0.0038 | 5.7 |

Figure 11:
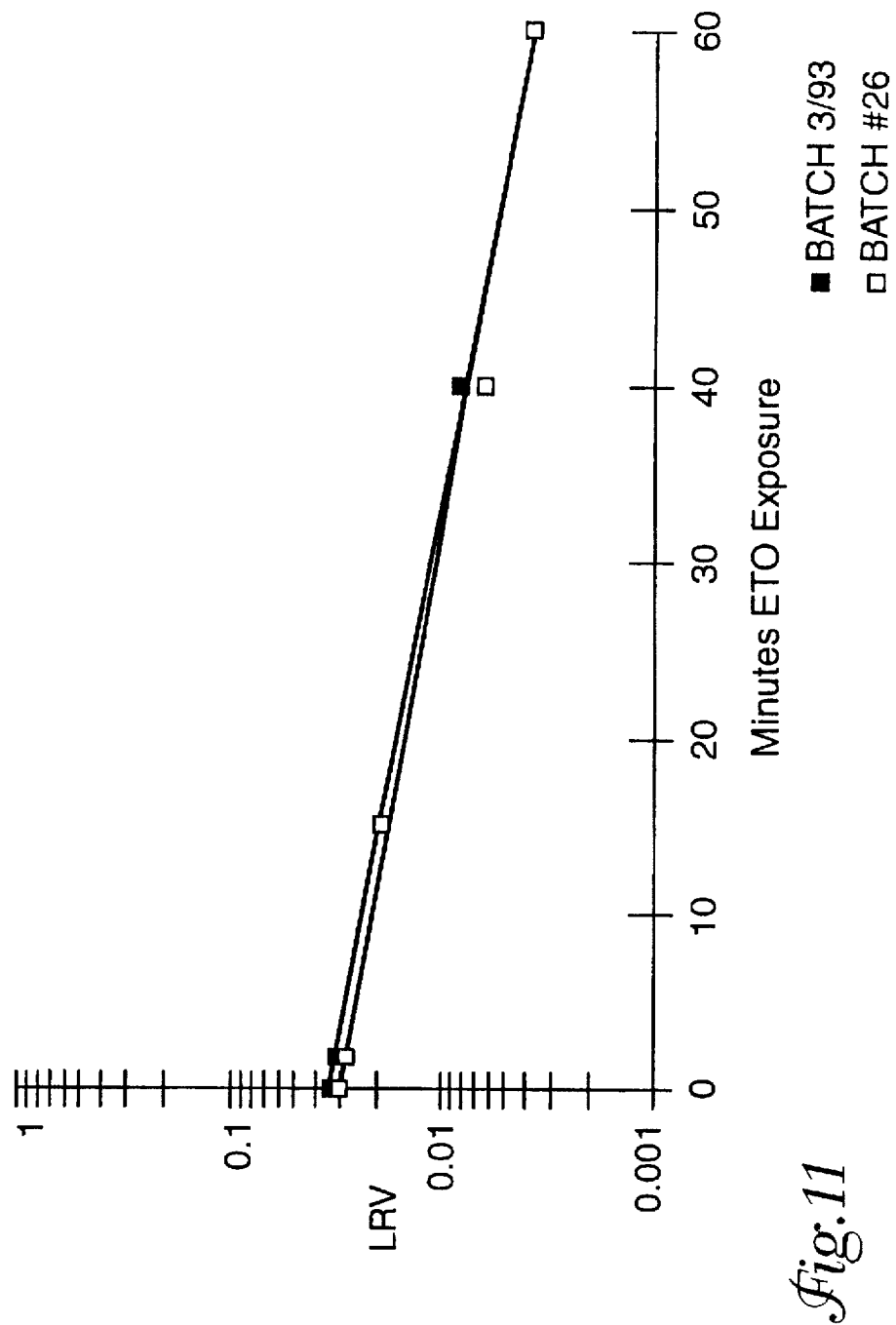
FIG. 11 is a graphical representation of the linear reaction velocities of two different batches of *Bacillus subtilis* spores.

There was essentially little or no difference between the two spore crops that were harvested one year apart in the LRV response before or after exposure to ETO. The standard deviation with batch 3/93 was greater than normally seen for the last three ETO exposure times. The LRV response of batch #26 was slightly lower at three of the ETO exposure times. This may have been due to the fact that batch #26 had been stored in a more dilute suspension than batch 3/93, and thus, had to be concentrated through centrifugation methods to bring the spore concentration up to the same level as in batch 3/93. In other experiments with batch #26, the LRV response was consistently slightly lower than with batch 3/93. Nevertheless, all other LRV characteristics were the same for both spore crops. Graphic representations of these results are shown in FIG. 11.

Example 9

Effect of a Hydrogen Peroxide Plasma Sterilization Cycle on the LRV Response of B. Subtilis Spores Eight semi-micro cuvettes with spores of B. subtilis were prepared as described in Example 4. Four of these cuvettes were placed inside a 3M STERI-LOK porous membrane bag (3M, St. Paul, Minn.) and closed with tape and the remaining four curvettes were set aside as the non-sterilized controls.

The four cuvettes in the bag were then subjected to a standard sterilization cycle with a load of medical devices in a STERRAD-100 Hydrogen Peroxide Plasma Sterilizer. The cycle was: Vacuum stage pressure —290 mtorr; injection stage pressure —7.23 torr; diffusion stage pressure —8.93 torr; and plasma stage pressure —502 mtorr. The elapsed time for this cycle was 1:10:20 hours.

After exposure to these sterilization conditions, the LRV of the spores in all eight cuvettes was determined using the procedure and the germination medium described in Example 4. The following results were obtained. The data are averages of four cuvettes for each treatment.

LRV of Non-Sterilized Controls=0.0443±0.001189 (2.7%)

LRV of Sterilized Spores=0.0048±0.000374 (3.7%)

This result indicates that sterilization conditions were achieved and that the LRV approach using spores of B. subtilis could be used to monitor the effectiveness of hydrogen peroxide plasma sterilization procedures.

Example 10
Determination of Germination Rates of *Bacillus Stearothermophilus* Spores The purpose of these experiments was to determine if it is feasible to measure germination rates of *Bacillus stearothermophilus* spores, and thus, if the LRV approach, as demonstrated with *B. subtilis*, could be used to monitor the sterilization effectiveness of procedures where the killing of microorganisms is accomplished using high temperature and pressure steam (autoclaves), heat, or low temperature steam formaldehyde (LTSF). *B. stearothermophilus* is the microorganism of choice for these procedures since it is a thermophile that grows optimally at temperatures of 55°–65° C.

Germination kinetics were determined spectrophotometrically at 480 nm wavelength of light, and the germination rates were determined from the decrease in absorbance using the polynomial regression equation $y=A0+A1x+A2x^2+\ldots$ In this equation, A1 is the slope of the regression line and thus the germination rate for the spores.

A volume of 0.1 ml of a spore suspension of *Bacillus stearothermophilus* strain DV296 (from culture collection of the School of Pharmacy and Pharmacology, University of Bath, Bath, U.K.) were added to 2.9 ml of the chemically defined growth (CDG) medium contained in quartz cuvettes preheated to 60° C. in the spectrophotometer. The CDG medium consisted of, per ml: 0.444 mg L-glutamine; 1.35 mg D-glucose; 0.497 mg $NH_4Cl$; 0.0027 mg $FeCl_3.6H_2O$; 0.0019 mg $MnCl_2.4H_2O$; 0.1016 mg $MgCl_2.6H_2O$; 0.011 mg $CaCl_2$; 0.01 $Na_2SO_4$; and 1/15 molar phosphate buffer adjusted to pH 7.0. The stock spore suspension contained $16-22\times10^8$ spores per ml, of which 16–21% germinated and were viable.

Table VI shows the effects of different amino acid germinants. All the amino acids used were the L-stereo isomers. These results indicate that it is feasible to determine germination rates of these spores, and thus, the LRV approach is expected to be useful to monitor the sterilization effectiveness.

TABLE VI

| Germination Medium | Germination Rate (Absorbance units/minute) ($\times 10^3$) |
|---|---|
| CDG | 4.4, 6.4, 7.5 |
| CDG minus glutamate, plus asparagine | 3.8 |
| CDG minus glutamate, plus alanine | 5.9 |
| CDG plus alanine | 5.5, 8.9 |

I claim:

1. A method of determining the effectiveness of a sterilization process comprising the steps of
   i) contacting an indicator comprising microbial spores with a sterilant to give exposed spores,
   ii) contacting the exposed spores with a medium selected to germinate the spores, and
   iii) calculating a rate of germination of the exposed spores to determine the effectiveness of the sterilization process.

2. The method of claim 1 wherein the sterilant is selected from the group consisting of steam, ethylene oxide, radiation, heat, sodium hypochlorite, polyvinylpyrrolidone-iodine, sodium dichlorocyanurate, low temperature steam-formaldehyde, glutaraldehyde and hydrogen peroxide, hydrogen peroxide plasma and mixtures thereof.

3. The method of claim 1 wherein the sterilant is ethylene oxide and the bacterial spores are spores of *Bacillus subtilis*.

4. A method of determining the effectiveness of a sterilization process comprising the steps of
   i) contacting an indicator comprising microbial spores with a sterilant to give exposed spores,
   ii) contacting the exposed spores with a medium selected to promote germination of the spores,
   iii) contacting germinating spores with a substrate selected to react with microbial metabolites from the germinating spores to provide a detectable indicator, and
   iv) detecting the presence of the detectable indicator to determine the effectiveness of the sterilization process.

5. A biological indicator system to determine the effectiveness of a sterilization process comprising:
   i) container means containing microbial spores and adapted to allow exposure of the spores to a sterilant as well as to allow exposed spores to contact a germination medium,
   ii) germination means adapted to contact the spores with the germination medium and incubate the spores at elevated temperatures, and
   iii) detection means adapted to measure the maximum germination rate for the incubated spores and provide an indication of the effectiveness of a sterilization cycle.

6. A biological indicator system to determine the effectiveness of a sterilization process comprising:
   i) container means containing microbial spores of *Bacillus subtilis* and adapted to allow exposure of the spores to a sterilant as well as to allow exposed spores to contact a germination medium wherein the container means is made of glass or a polymer selected from the group consisting of poly(methyl methacrylate) and polystyrene that is transparent to light,
   ii) germination means comprising a medium containing nutrient, ions, and a germinant selected from the group consisting of L-asparagine and L-glutamine, wherein said germination means is adapted to contact the spores with the germination medium and incubate the spores at elevated temperatures, and
   iii) detection means adapted to measure the maximum germination rate for the incubated spores and provide an indication of the effectiveness of a sterilization cycle wherein the detection means comprises an absorbance spectrophotometer or nephelometer.

* * * * *